(12) United States Patent
Chen et al.

(10) Patent No.: US 8,229,573 B2
(45) Date of Patent: Jul. 24, 2012

(54) SPRING PASSIVE LEAD ANCHOR AND METHODS AND DEVICES USING THE ANCHOR

(75) Inventors: Roger Chen, Castaic, CA (US); John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 237 days.

(21) Appl. No.: 12/506,880

(22) Filed: Jul. 21, 2009

(65) Prior Publication Data

US 2011/0022141 A1  Jan. 27, 2011

(51) Int. Cl.
*A61N 1/04* (2006.01)
(52) U.S. Cl. ......... 607/130; 607/117; 607/126; 600/386
(58) Field of Classification Search .................. 607/116, 607/117, 130, 132, 30; 600/386, 390
See application file for complete search history.

(56) References Cited

U.S. PATENT DOCUMENTS

| | | | | |
|---|---|---|---|---|
| 4,126,918 A | * | 11/1978 | Cornell | 24/132 R |
| 4,374,527 A | * | 2/1983 | Iversen | 607/117 |
| 4,419,819 A | | 12/1983 | Dickhudt et al. | |
| 4,453,292 A | * | 6/1984 | Bakker | 24/115 G |
| 5,273,053 A | | 12/1993 | Pohndorf | |
| 5,476,493 A | | 12/1995 | Muff | |
| 5,628,780 A | * | 5/1997 | Helland et al. | 607/126 |
| 5,727,847 A | * | 3/1998 | Martone et al. | 297/375 |
| 5,823,020 A | * | 10/1998 | Benda | 70/18 |
| 5,843,146 A | | 12/1998 | Cross, Jr. | |
| 6,181,969 B1 | | 1/2001 | Gord | |
| 6,473,654 B1 | | 10/2002 | Chinn | |
| 6,516,227 B1 | | 2/2003 | Meadows et al. | |
| 6,609,029 B1 | | 8/2003 | Mann et al. | |
| 6,609,032 B1 | | 8/2003 | Woods et al. | |
| 6,741,892 B1 | | 5/2004 | Meadows et al. | |
| 7,244,150 B1 | | 7/2007 | Brase et al. | |
| 2003/0114905 A1 | | 6/2003 | Kuzma | |
| 2004/0059392 A1 | | 3/2004 | Parramon et al. | |
| 2005/0051385 A1 | * | 3/2005 | Klingler | 182/5 |
| 2005/0165465 A1 | | 7/2005 | Pianca et al. | |

(Continued)

FOREIGN PATENT DOCUMENTS

EP   625359 A2   11/1994

(Continued)

OTHER PUBLICATIONS

U.S. Appl. No. 11/238,240, filed Sep. 29, 2005.

*Primary Examiner* — Carl H Layno
*Assistant Examiner* — Eugene Wu
(74) *Attorney, Agent, or Firm* — Frommer Lawrence & Haug LLP; Bruce E. Black

(57) ABSTRACT

A lead anchor includes a body defining at least one first portion of a lead lumen, the body having a first opening and a second opening. An obstructing member is disposed within the body. The obstructing member defines a second portion of the lead lumen. A spring is disposed in the body and configured and arranged to operate on the obstructing member so that the second portion of the lead lumen is coterminous with the at least one first portion of the lead lumen and forms a continuous lead path when the spring is compressed and the second portion of the lead lumen is offset from the at least one first portion of the lead lumen when the spring is not compressed.

15 Claims, 11 Drawing Sheets

U.S. PATENT DOCUMENTS

2007/0050005 A1 3/2007 Lauro
2007/0150007 A1 6/2007 Anderson et al.
2007/0150036 A1 6/2007 Anderson
2007/0161294 A1 7/2007 Brase et al.
2007/0219595 A1 9/2007 He
2007/0239243 A1 10/2007 Moffitt et al.
2008/0071320 A1 3/2008 Brase
2008/0243220 A1 10/2008 Barker
2009/0254151 A1 10/2009 Anderson et al.

FOREIGN PATENT DOCUMENTS

EP 988080 B1 2/2007
WO 98/48880 A1 11/1998
WO 2008121708 A2 10/2008

* cited by examiner

US 8,229,573 B2

SPRING PASSIVE LEAD ANCHOR AND METHODS AND DEVICES USING THE ANCHOR

FIELD

The invention is directed to lead anchors for implantable devices, as well as the implantable devices themselves, and methods of manufacture and use of the lead anchors and implantable devices. The present invention is also directed to lead anchors having a spring and an obstructing member as well as methods of making and using the leads and electrical stimulation systems.

BACKGROUND

Spinal cord stimulation is a well accepted clinical method for reducing pain in certain populations of patients. Implantable stimulation devices have been developed to provide therapy for a variety of treatments. For example, implantable stimulation devices can be used to stimulate nerves, such as the spinal cord, muscles, or other tissue. An implantable stimulation device typically includes an implanted control module (with a pulse generator), a lead, and an array of stimulator electrodes. The stimulator electrodes are implanted in contact with or near the nerves, muscles, or other tissue to be stimulated. The pulse generator in the control module generates electrical pulses that are delivered by the electrodes to body tissue. As an example, electrical pulses can be provided to the dorsal column fibers within the spinal cord to provide spinal cord stimulation.

The stimulator electrodes are coupled to the control module by the lead and the control module is implanted elsewhere in the body, for example, in a subcutaneous pocket. The lead is often anchored at one or more places in the body to prevent or reduce movement of the lead or stimulator electrodes within the body which could damage tissue, move the stimulator electrodes out of the desired position, or interrupt the connection between the stimulator electrodes and the control module.

Many conventional lead anchors possess inadequate lead retention strength when the lead is subjected to tensile loading. This may cause the lead to migrate proximally from the desired neurostimulation site. According to recent studies, lead migration occurs in approximately 13% of cases. Additional studies suggest that electrode migration may be the most common reason for failure to maintain long-term pain control with spinal cord stimulation. Other problems associated with lead migration include lead breakage, and loose connection.

Yet another problem associated with conventional lead anchors is that most anchors depend heavily on suturing techniques and thus have variable holding forces. The added suturing not only leads to inconsistent lead retention but also unnecessarily increases the time in the operating room.

BRIEF SUMMARY

In one embodiment, a lead anchor includes a body defining at least one first portion of a lead lumen, the body having a first opening and a second opening. An obstructing member is disposed within the body, the obstructing member defining a second portion of the lead lumen. A spring is disposed in the body and configured and arranged to operate on the obstructing member so that the second portion of the lead lumen is coterminous with the at least one first portion of the lead lumen and forms a continuous lead path when the spring is compressed. The second portion of the lead lumen is offset from the at least one first portion of the lead lumen when the spring is not compressed.

In another embodiment, a method of implanting an implantable stimulation device includes implanting a portion of a lead having an electrode array near tissue to be stimulated. A force is applied to an obstructing member of a lead anchor. The lead anchor includes a body defining at least one first portion of a lead lumen, the body having a first opening and a second opening. The obstructing member defines a second portion of the lead lumen. A spring is disposed in the body and configured and arranged to operate on the obstructing member so that the second portion of the lead lumen is coterminous with the at least one first portion of the lead lumen and forms a continuous lead path when the spring is compressed and the second portion of the lead lumen is offset from the at least one first portion of the lead lumen when the spring is not compressed. A lead is placed through the lead path and the force is released on the obstructing member so that the lead path locks a portion of the lead with the lead anchor. The lead anchor is secured to the surrounding tissue using sutures.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of lead anchors used with elongate implantable devices such as spinal cord leads, cardiac pacing leads or catheters, implantable devices or systems containing the lead anchors, methods of use and manufacture of lead anchors and implantable devices. In addition, the invention is directed to lead anchors for implantable spinal cord stimulators, as well as the stimulators themselves and methods of use and manufacture of the lead anchors and spinal cord stimulators.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
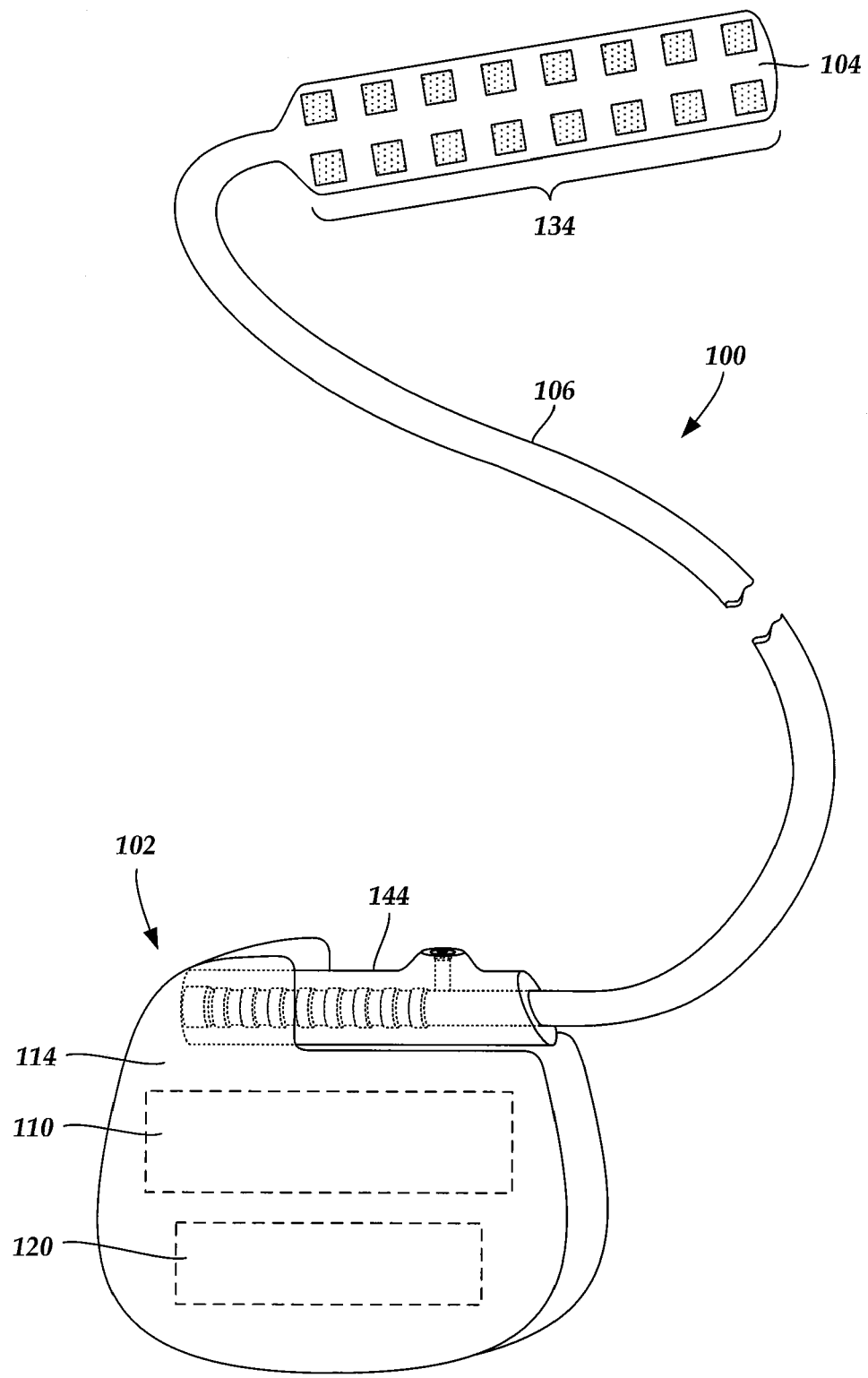
FIG. 1 is a schematic perspective view of one embodiment of an electrical stimulation system, according to the invention.
Figure 2:
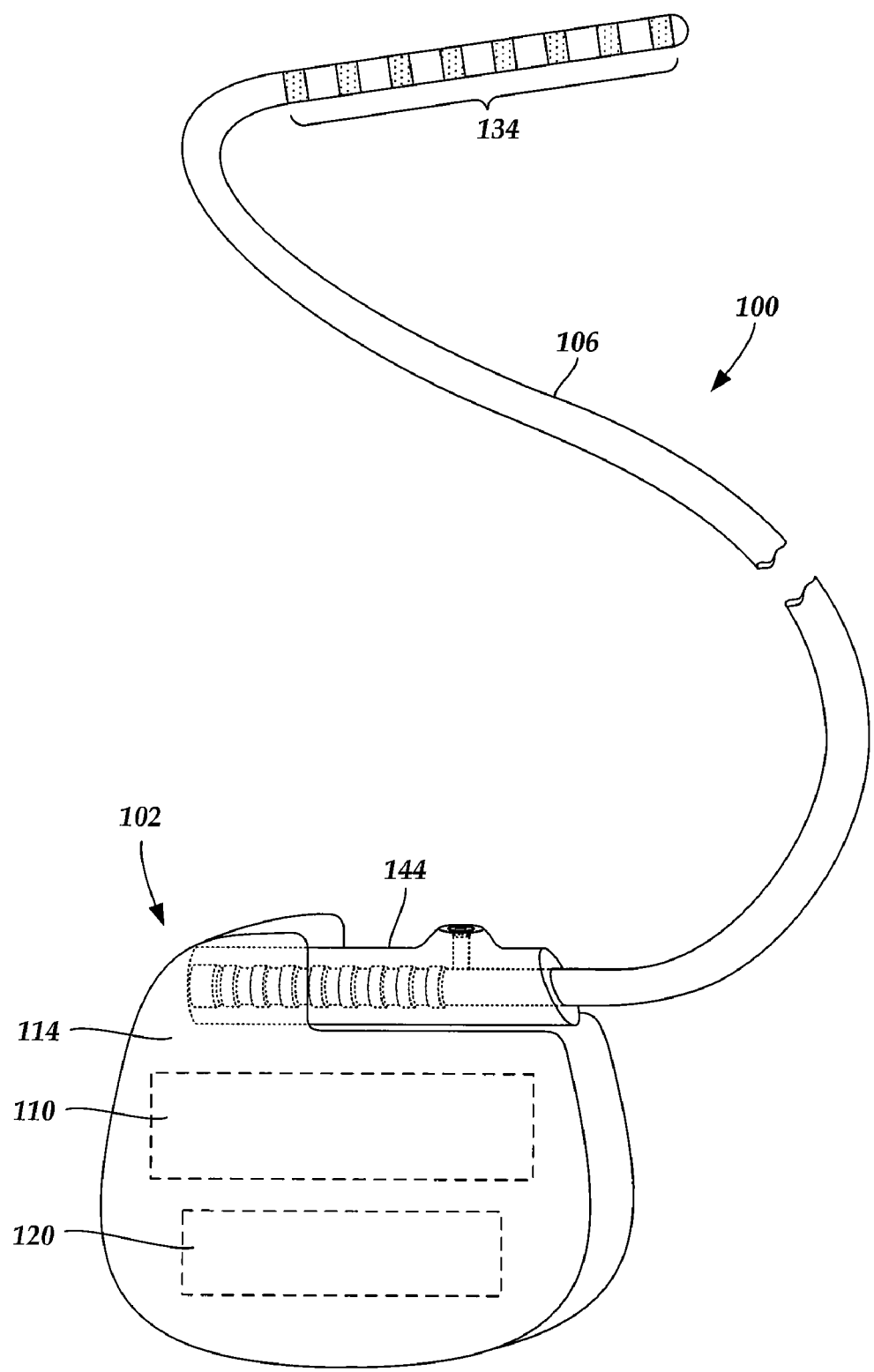
FIG. 2 is a schematic perspective view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via connector contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone, epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding connector contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as connector contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductors may be embedded in the non-conductive material of the lead or can be disposed in one or more lumens (not shown) extending along the lead. In some embodiments, there is an individual lumen for each conductor. In other embodiments, two or more conductors may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
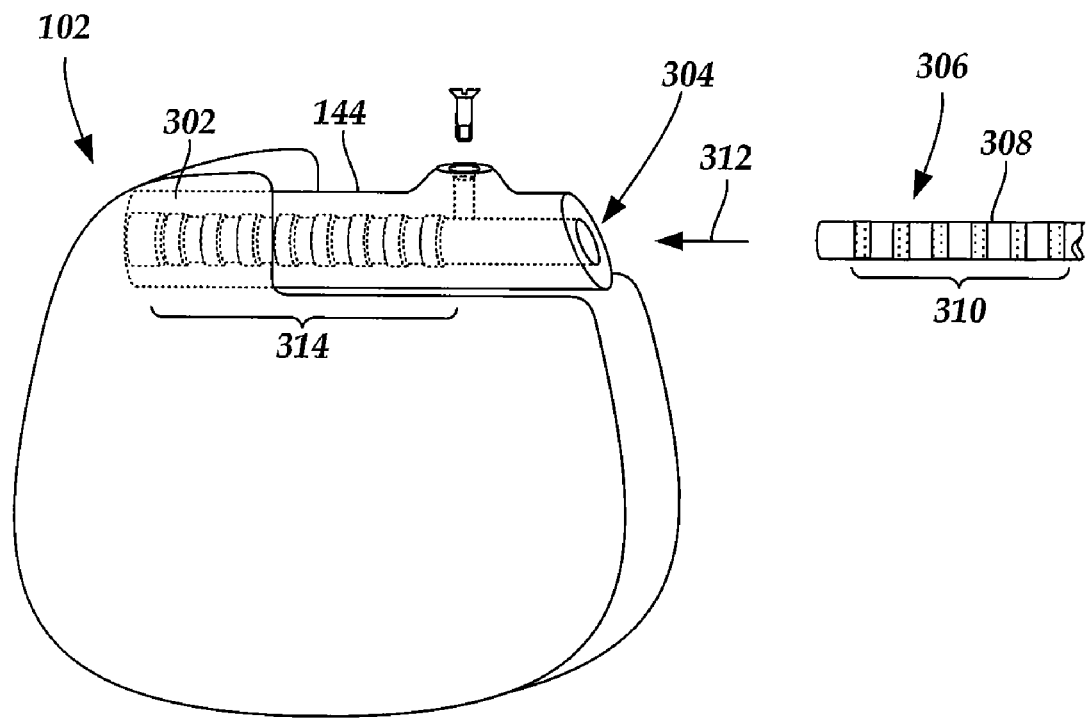
FIG. 3A is a schematic perspective view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of connector contacts 314 for each port 304. When the lead 308 is inserted into the port 304, the connector contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
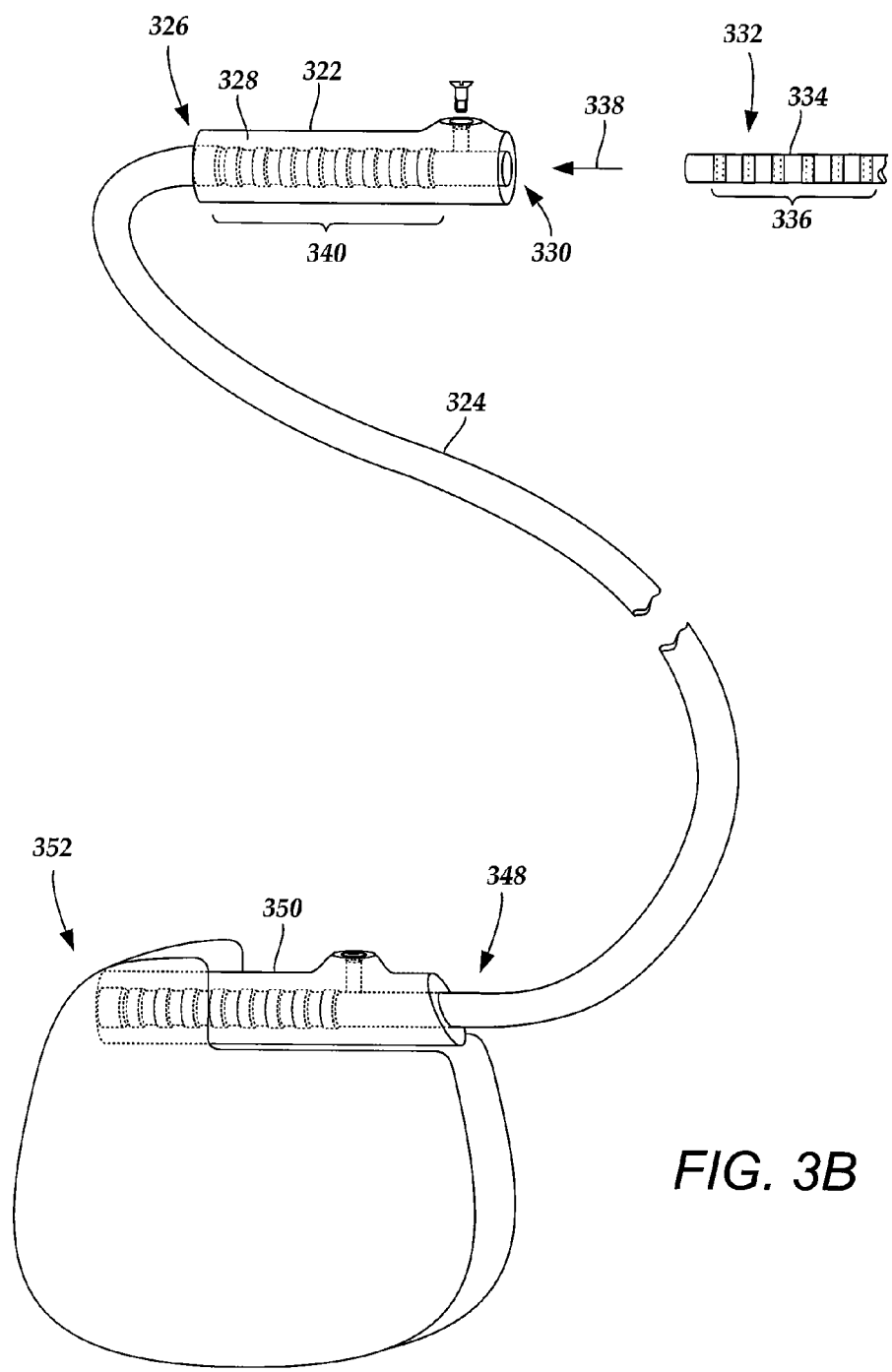
FIG. 3B is a schematic perspective view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of connector contacts 340. When the lead 334 is inserted into the port 330, the connector contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductors (not shown) that electrically couple the connector contacts 340 to a proximal end 348 of the lead extension 324 that is opposite to the distal end 326. In at least some embodiments, the conductors disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

A lead anchor can be used in, or with, an implantable device, such as an implantable spinal cord stimulator, to anchor a lead connecting a control module to an electrode array. The lead anchor includes a body, an obstructing member and a spring. In at least some embodiments, the lead anchor also contains a suture element disposed on the body.

Figure 4:
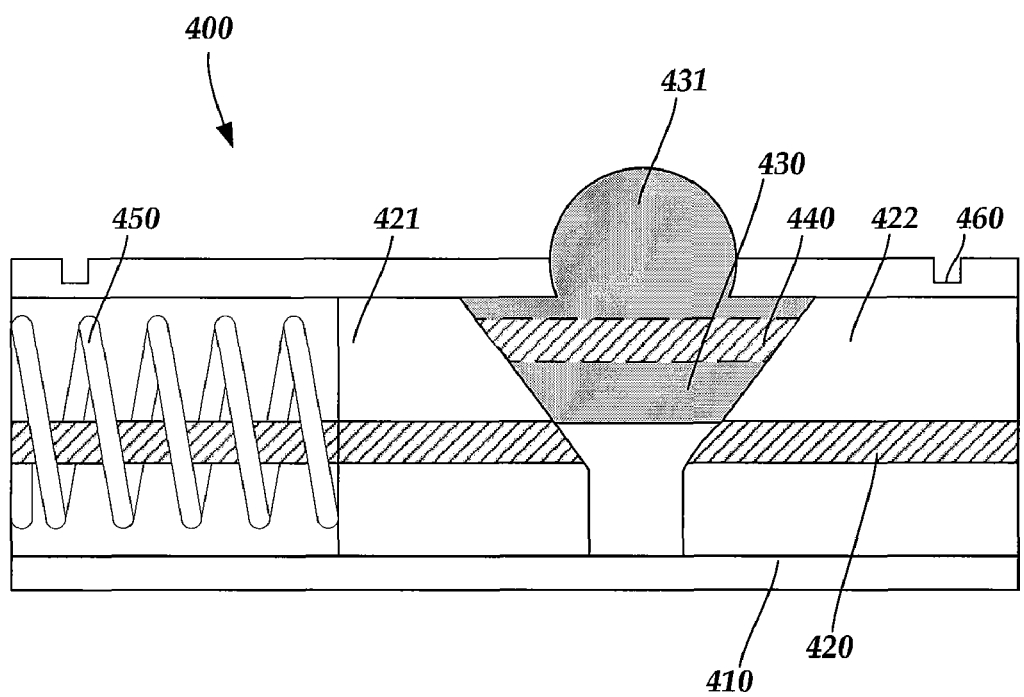
FIG. 4 is a schematic perspective view of one embodiment of a spring passive anchor, before the spring has been compressed, according to the invention.

FIG. 4 is a schematic perspective view of one embodiment of a spring passive anchor 400. The spring passive anchor 400 includes a body 410, an obstructing member 430 and a spring 450. The body 410 may be made of a metal, such as titanium, nickel, aluminum, stainless steel, copper, gold, silver, platinum and alloys thereof or any other biocompatible metal, or a rigid plastic or polymer material. It is contemplated that the body 410 may be formed of any shape. In some embodiments, the body 410 is a cuboid, a cube, a cylinder, a triangular prism, a rectangular prism, a parallelepiped, a sphere, or any other shape suitable for use as the body of an anchor.

The body 410 defines a lead lumen 420 through which a lead (not shown) may pass. The lead lumen 420 may have a cross-section that is substantially circular as it extends from one end to the other. It is contemplated that the lead lumen 420 may also have a cross-section in the shape of a triangle, a square, an ovoid, or any other suitable shape that is large enough to house the lead. In some embodiments the lead lumen 420 may be defined so that the lead passes along a straight path through the center of the body 410. Conversely the lead lumen 420 may be defined so that the lead passes at an angled path through the body 410. In some embodiments, the lead lumen 420 is defined as a curved path through the body 410. In at least some embodiments, the body 410 contains more than one lead lumen so that the spring passive anchor 400 is able to house more than one lead. The lead lumen may be large enough to allow the lead to pass through freely.

In some embodiments, the body 410 includes lead carriers 421 and 422. A lead carrier may be a cuboid, a cube, a cylinder, a triangular prism, a rectangular prism, a parallelepiped, a sphere, or any other shape suitable for being disposed within the body 410. In some embodiments, the body 410 includes a single lead carrier. As seen in FIG. 4, in at least some other embodiments, a plurality of lead carriers are disposed within the body 410. In some embodiments, a plurality of lead carriers are disposed within the body 410 and at least one of the lead carriers disposed within the body 410 is capable of a movement, a translation, or a rotation within the body 410. The lead lumen 420 may also be disposed within at least one of the lead carriers.

As seen in FIG. 4, an obstructing member 430 may be disposed within the body 410. As with the body 410, it is also contemplated that the obstructing member 430 may be formed in any shape capable of being disposed within the body 410. In some embodiments, the obstructing member 430 may be substantially a trapezoidal prism, a rectangular prism, a parallelepiped, a cuboid, a cube, a cylinder, an ovoid, a sphere, or any other shape suitable for being disposed within the body 410.

A lead lumen 440 may be defined by the obstructing member 430. The lead lumen 440 may have a cross-section in any shape as discussed with reference to the lead lumen 420 (i.e. triangular, square, ovoid, etc.). The lead lumen 440 may also be a straight or curved path within the obstructing member 430. In some embodiments, the lead lumen 440 is substantially similar to the lead lumen 420 in shape, size, or curvature, or any combination thereof. In embodiments containing multiple lead lumens, multiple lead lumens may be provided within the obstructing member 430. In at least some other embodiments, a single lead lumen is defined within each of a plurality of obstructing members 430. These may also be combinations of obstructing members with multiple lead lumens and obstructing members with single lead lumens. The lead lumen 440 may be disposed in the obstructing member 430 such that it is not coterminous with the lead lumen 420 when a spring 450 is in its uncompressed state. In some embodiments, the first portion of the lead 440 is offset of the lead lumen 420 when the spring 450 is uncompressed. In some other embodiments, the first portion of the lead 440 is staggered or at an angle to the lead lumen 420 when the spring 450 is uncompressed.

The obstructing member 430 is coupled to an actuator 431. The actuator 431 may be any member, coupled or coupleable to the obstructing member 430, that facilitates the movement or actuation of the obstructing member 430 relative to lead carriers 421 and 422. In some embodiments, as depicted in FIG. 4, the actuator 431 and the obstructing member 430 are unitary. The actuator 431 may also be a depression, dent, or concavity within the obstructing member 430 that facilitates the actuating of the obstructing member 430. In some embodiments, the actuator 431 may be pressed down to actuate the obstructing member 430. In some other embodiments, the actuator 431 is engaged by a toggle, twist, pull, or any other suitable actuating method.

The body 410 also houses a spring 450. The spring 450 may be made of annealed steel, titanium, or any other biocompatible metal. Furthermore, the spring 450 may be any elastic member capable of storing mechanical energy. Suitable springs include, but are not limited to cantilever springs, coil or helical springs, leaf springs, or any other spring or bias suitable for operating on the obstructing member 430 as will be understood with reference to FIG. 5. Thus, the size, shape and spring constant of the spring 450 may vary. The displacement or deformation of the spring 450 may also vary. For example, in some embodiments, the spring 450 may be displaced to ¾, ⅔, ½, ⅓ or ¼ of its original length.

Figure 5:
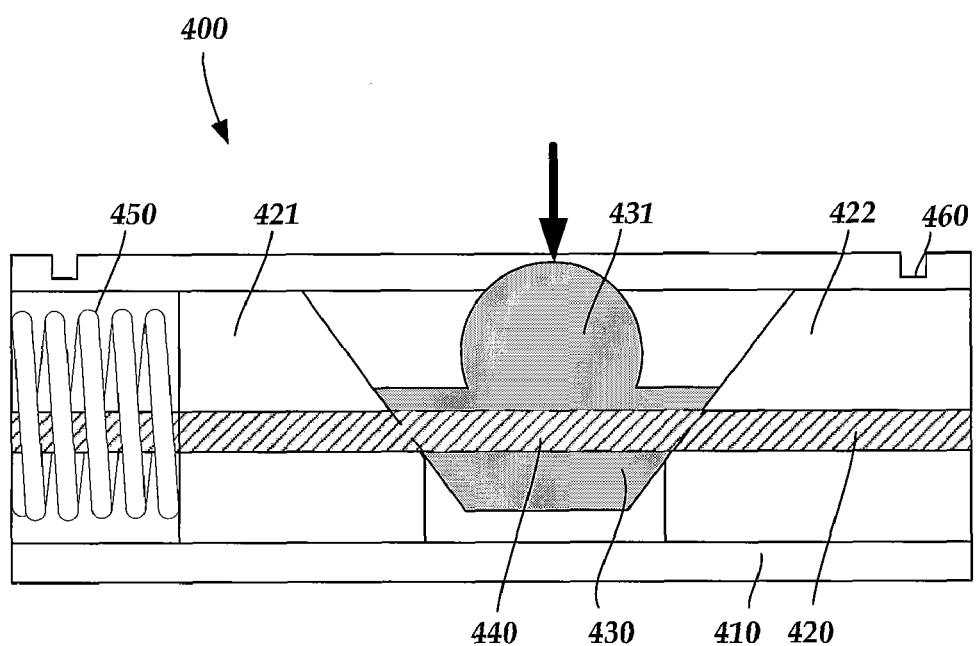
FIG. 5 is a schematic perspective view of the spring passive anchor of FIG. 4, after the spring has been compressed, according to the invention.

The spring 450 may disposed in a variety of locations within the body 410. In some embodiments, the spring 450 is disposed in a corner of the body 410. In at least some other embodiments, the spring 450 is disposed in the center of the body 410, or to one side of the body 410. In at least some embodiments, the spring 450 is disposed within the body 410 so as to lie adjacent to one side of the obstructing member 430. In at least some other embodiments, the spring 450 is disposed apart from the obstructing member 430. The spring 450 may also be disposed next to any portion of the body 410. For example, in some embodiments, the spring 450 is disposed to one side of the body 410, parallel to the lead lumen 420. As seen in FIGS. 4 and 5, the spring 450 may also be disposed around a portion of the lead lumen 420. This embodiment may be referred to as the "inline spring." By placing the spring 450 inline with the lead lumen 420, the spring passive anchor 400 is able to have a smaller diameter.

Furthermore, it may be useful for any or all parts of the spring passive anchor to be made of a material that is radiopaque, so that it is visible under fluoroscopy or other forms of x-ray diagnosis. In some embodiments, any of the body, the obstructing member, the spring, or any combination thereof is radiopaque so as to allow the lead anchor to be readily identified under fluoroscopy or other forms of x-ray diagnosis. Moreover, in some embodiments, the lead is radiopaque.

Suture elements 460 may also be disposed on the body 410. In at least some embodiments, the body 410 may define a plurality of suture elements. The suture element 460 may be a groove, stub, ridge, eyelet, opening or bore or any other suitable arrangement for suturing the spring passive lead anchor 400 to the fascia, ligament or other tissue or body structure. The suture element 460 may be positioned anywhere on the body 410. For example, the suture elements 460 may be disposed on the corners of the body 410, through the center of the body 410, or at various increments along the circumference of the body 410.

FIG. 5 is a schematic perspective view of the spring passive anchor of FIG. 4, after the spring 450 has been compressed. In some embodiments, as illustrated in FIG. 5, actuating the actuator 430 causes the obstructing member 430 to press down against lead carriers 421 and 422. In turn, the carrier body 421 is able to overcome the spring force and compress the spring 450. In some embodiments, by actuating the actuator 431, or directly actuating the obstructing member 430, any number of lead carriers are translated or pushed apart. When the spring 450 is compressed, the spring passive anchor 400 is placed in an open position. In some embodiments, this open position of the spring passive anchor 400 is accomplished when the obstructing member 430 is translated into a position such that the lead lumen 420 and the first portion of the lead lumen 440 become aligned and coterminous, forming a continuous lead path throughout the body 410 of the spring passive anchor 400. In at least some embodiments, the open position requires that the physician continuously actuate the actuator 431, i.e. that the spring passive anchor 400 returns to a closed position when the actuator 431 is not actuated. When the continuous lead path is formed, the physician may then load the lead into the anchor 400 (e.g. slide the spring passive anchor 400 along the length of the lead). Once the physician releases the actuator 431, the spring 450 forces the spring passive anchor 400 to return to the locked position, thereby securing the lead to the lead. The physician may then secure the spring passive anchor 400 to the patient tissue using sutures.

Figure 6:
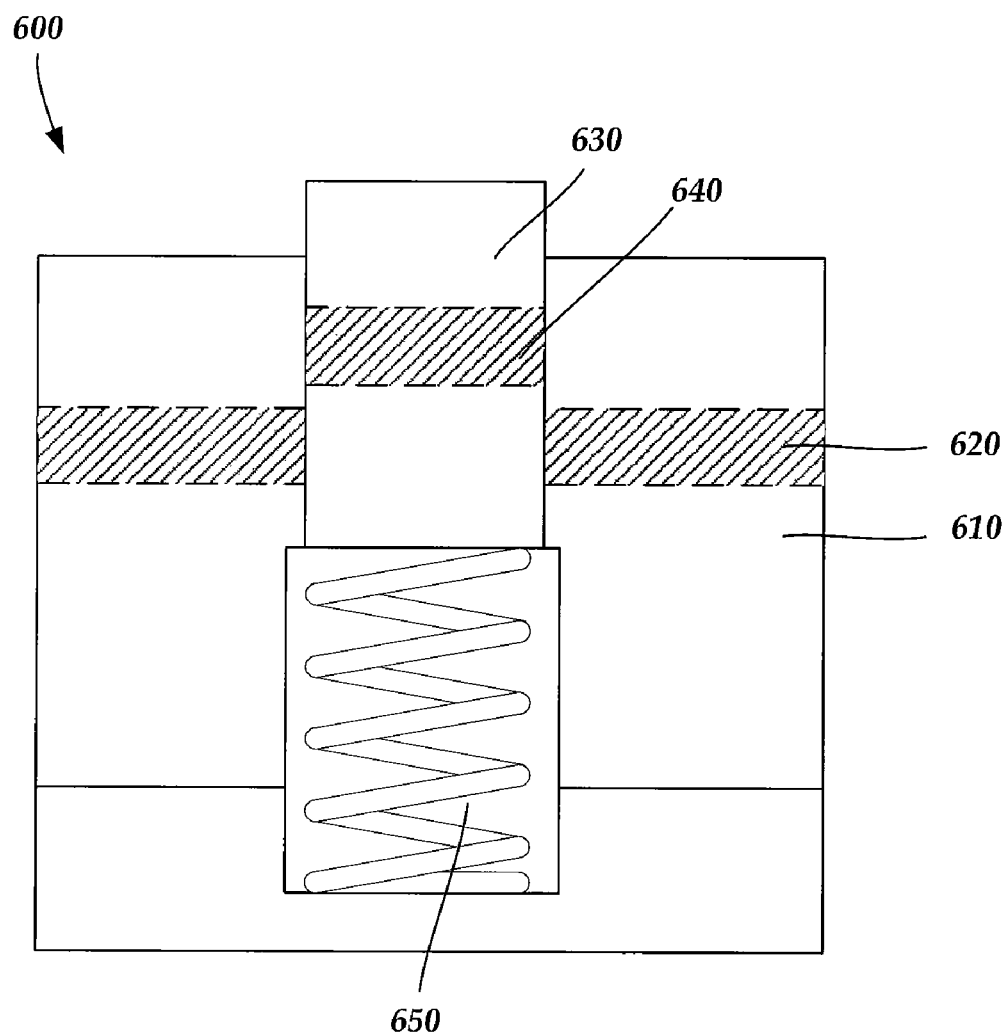
FIG. 6 is a schematic perspective view of another embodiment of a spring passive anchor, before the spring has been compressed, according to the invention.

FIG. 6 is a schematic perspective view of another embodiment of a spring passive anchor. The configuration of FIG. 6 includes a body 610 having a lead lumen 620, and an obstructing member 630 having a first portion of the lead lumen 640. As previously noted, a spring may be disposed anywhere within the body. As seen in FIG. 6, the spring 650 is disposed perpendicular to the lead lumen 620, and coupled to the obstructing member 630. This embodiment may be referred to as the "perpendicular spring" configuration. By placing the spring 650 perpendicular to the lead lumen 620, a shorter spring passive anchor 600 may be formed. In some embodiments, the first portion of the lead lumen 640 and the lead lumen 620 are not aligned when the spring is in its uncompressed state.

Figure 7:
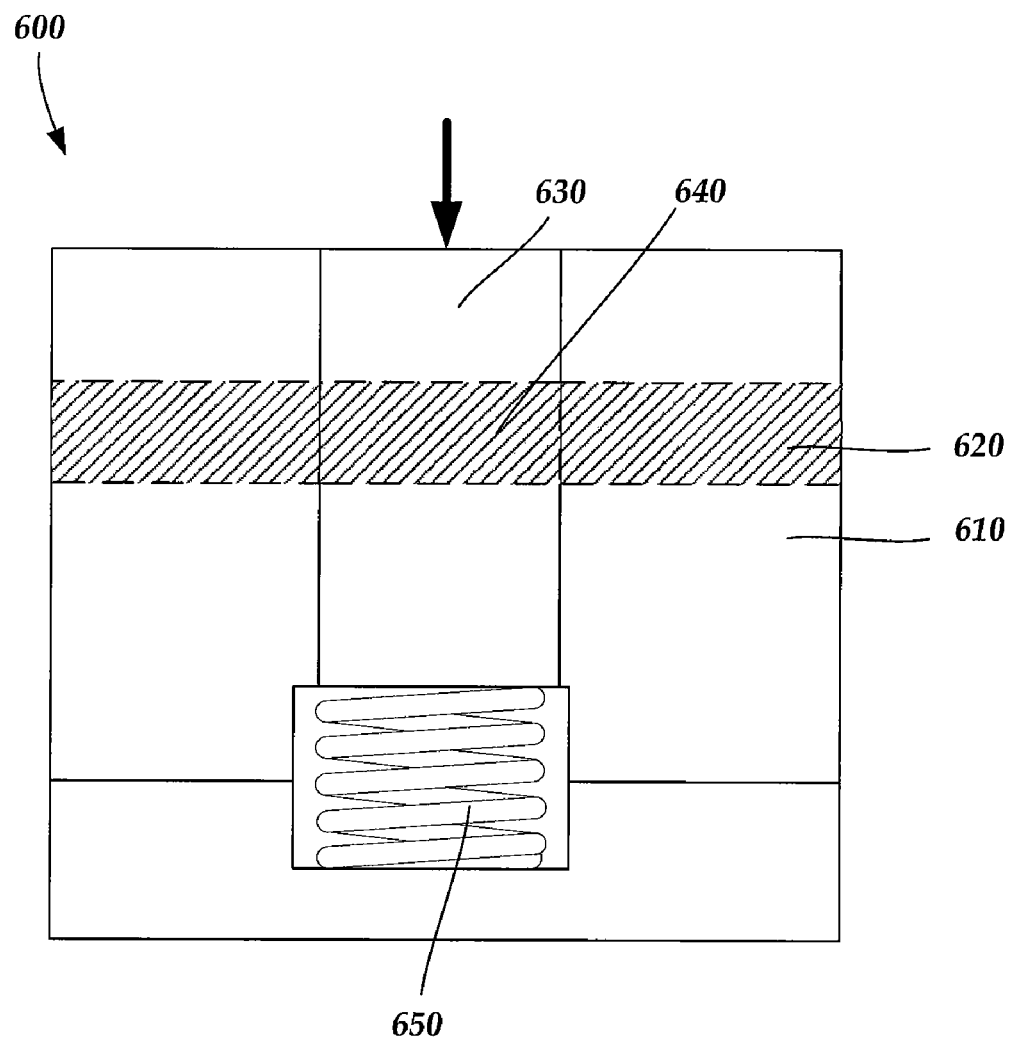
FIG. 7 is a schematic perspective view of the spring passive anchor of FIG. 6, after the spring has been compressed, according to the invention.

FIG. 7 is a schematic perspective view of the spring passive anchor of FIG. 6, after the spring has been compressed. As seen in FIG. 7, when the obstructing member 630 is pressed, the spring 650, located beneath the obstructing member 630, is compressed. The force needed to compress the spring 650 may vary. In some embodiments, the force needed to overcome the spring force will be small enough that it can be manually overcome by a physician, but large enough to properly secure the lead. When the obstructing member 630 has been compressed, a single continuous path is formed throughout the body 610. The physician may then insert the lead through the spring passive anchor 600, and release the force on the obstructing member 630 so that the lead is secured. Additionally, the physician may also suture the spring passive anchor to patient tissue using sutures disposed on the body 610.

Figure 8A:
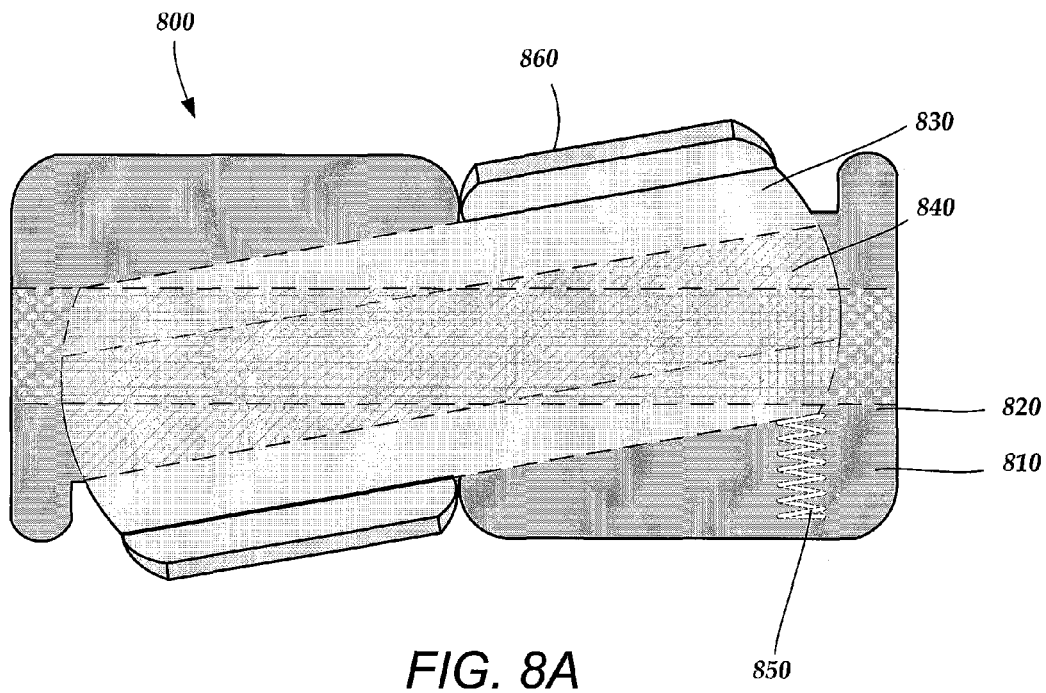
FIG. 8A is a schematic perspective view of a third embodiment of a spring passive anchor, before the spring has been compressed, according to the invention.

FIG. 8A is a schematic perspective view of a third embodiment of a spring passive anchor. The embodiment of FIG. 8A, which may be referred to as the "rotating member anchor," utilizes many of the same methods discussed above. A spring passive anchor 800 includes a body 810, an obstructing member 830, and a spring 850. An optional base 860 may be disposed within the body 810 to support the spring 850. The body 810 defines a lead lumen 820. Though FIG. 8A depicts a lead lumen 820 going through the center of the body 810, it will be understood that the shape, path and location of the lead lumen 820 may vary as discussed above. In FIG. 8A, the obstructing member 830 is in the form of a substantially cylindrical rotating arm disposed within the body 810. The obstructing member 830 also includes a first portion of the lead lumen 840. As can be appreciated from FIG. 8A, the obstructing member 830 is disposed within the body 810 so that it is able to rotate or swivel about an axis of rotation 860. In some embodiments, the axis of rotation is optionally provided with a pin, dowel, rivet, swivel or any other structure suitable for facilitating rotation of the obstructing member 830.

Figure 8B:
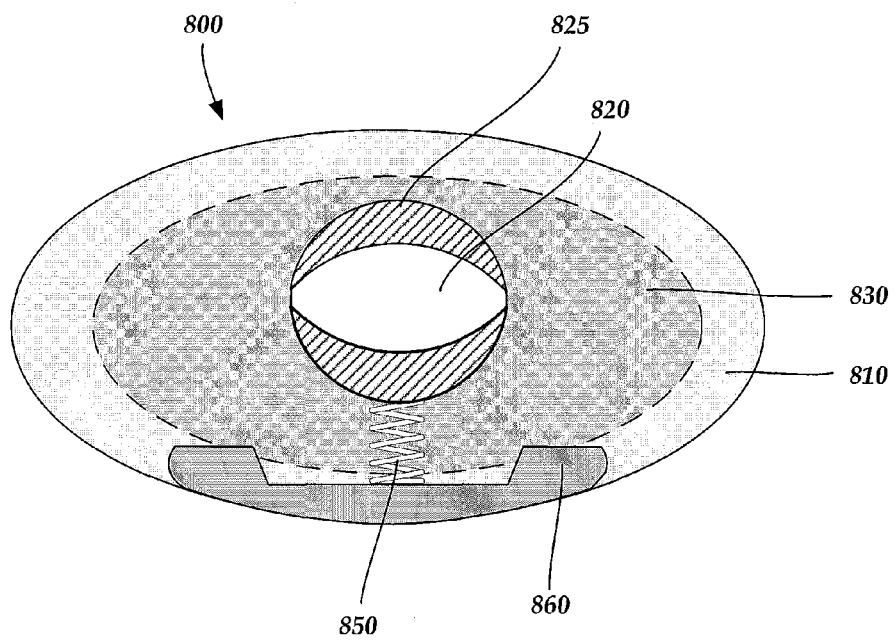
FIG. 8B is a schematic side view of the spring passive anchor of FIG. 8A, before the spring has been compressed, according to the invention.

FIG. 8B is a schematic side view of the spring passive anchor 800 of FIG. 8A. At rest, while the spring 850 is uncompressed, portions of the lead lumen 820 are obstructed by the obstructing member 830. As seen in FIG. 8B, when the anchor is in a closed position, the obstructing portions 825 prevent a lead from passing through the body 810.

Figure 9A:
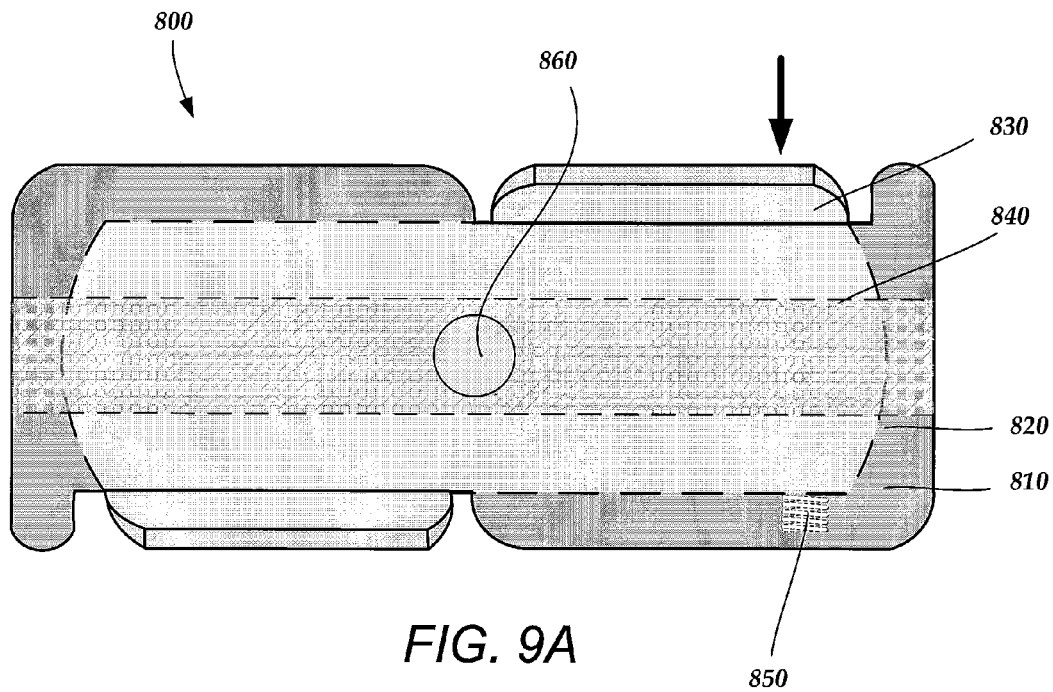
FIG. 9A is a schematic perspective view of the spring passive anchor of FIG. 8, after the spring has been compressed, according to the invention.
Figure 9B:
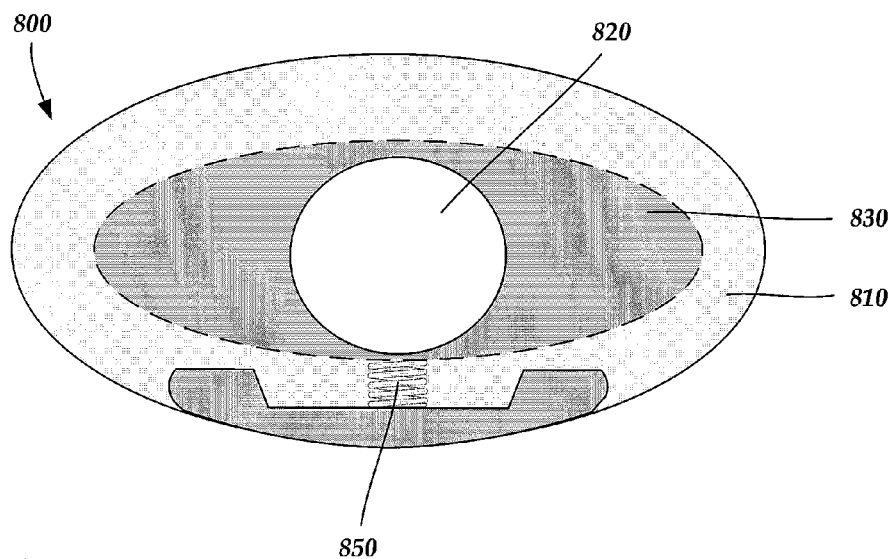
FIG. 9B is a schematic side view of the spring passive anchor of FIG. 9A, after the spring has been compressed, according to the invention.

FIG. 9A is a schematic perspective view of the spring passive anchor 800 of FIG. 8, after the spring 850 has been compressed. As seen in FIG. 9A, when a force is applied to the obstructing member 830 to overcome the spring force, the obstructing member 830 rotates about the axis of rotation 860 into a position where the lead lumen 820 and the first portion of the lead lumen 840 are aligned. FIG. 9B is a schematic side view of the spring passive anchor 800 of FIG. 9A, depicting a continuous lead path through the center of the body 810. As seen in FIG. 9A, when the obstructing member 830 has been actuated, and the spring 850 has been compressed, a continuous, coterminous path exists from one end of the body 810 to the other end of the body 810. In at least some embodiments, an actuator (not shown) is disposed on the obstructing member 830 to assist in rotating the obstructing member 830 within the body 810. When the obstructing member 830 has been rotated to the correct position, a lead may then be placed through the continuous lead path.

After a lead has been placed through the lead lumen 820, the force on the obstructing member 830 is released. The compressed spring 850 forces the obstructing member 830 to rotate about the axis of rotation 860. The force of the spring 850 effectively locks the lead in position. The physician may optionally suture the spring passive anchor 800 to patient tissue using sutures disposed on the body 810.

Figure 10:
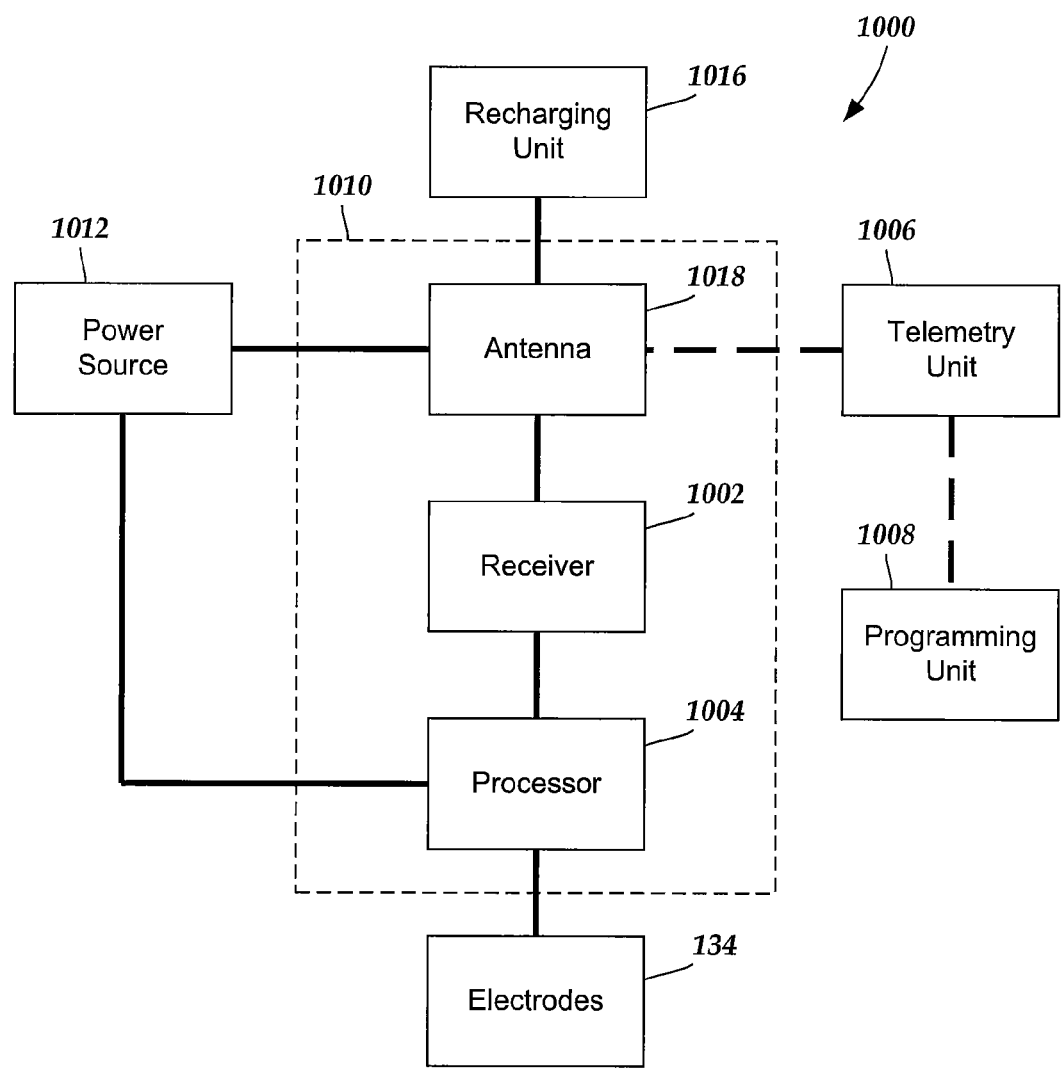
FIG. 10 is a schematic perspective overview of one embodiment of components of an electrical stimulation system, including an electronic subassembly disposed within a control module, according to the invention.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, power source 1012, antenna 1018, receiver 1002, and processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In at least one embodiment, electrical current is emitted by the electrodes 134 on the paddle or lead body to stimulate nerve fibers, muscle fibers, or other body tissues near the electrical stimulation system. A processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 may select which electrode(s) are cathodes and which electrode(s) are anodes. In some embodiments, the processor 1004 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by a programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include an antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of implanting an implantable stimulation device, the method comprising:
   implanting a portion of a lead having an electrode array near tissue to be stimulated;
   applying a force to an obstructing member of a lead anchor, the lead anchor comprising a body defining at least one first portion of a lead lumen, the body having a first opening and a second opening, the obstructing member defining a second portion of the lead lumen, a spring disposed in the body and configured and arranged to operate on the obstructing member so that the second portion of the lead lumen is coterminous with the at least one first portion of the lead lumen and forms a continuous lead path when the spring is compressed and the second portion of the lead lumen is offset from the at least one first portion of the lead lumen when the spring is not compressed, wherein applying a force to an obstructing member comprises rotating the obstructing member to compress the spring;
   placing a lead through the lead path;
   releasing the force on the obstructing member so that the lead path locks a portion of the lead with the lead anchor;
   securing the lead anchor to the surrounding tissue using sutures.

2. The method of claim 1, further comprising implanting a control module and coupling the electrode array to the control module using a lead.

3. The method of claim 1, wherein applying a force to an obstructing member comprises actuating an actuator.

4. A lead anchor, comprising:
   a body defining at least one first portion of a lead lumen, the body having a first opening and a second opening;
   an obstructing member disposed within the body, the obstructing member defining a second portion of the lead lumen, wherein the obstructing member comprises a rotating member arm;
   a spring disposed in the body and configured and arranged to operate on the obstructing member so that the second portion of the lead lumen is coterminous with the at least one first portion of the lead lumen and forms a continuous lead path when the spring is compressed and the second portion of the lead lumen is offset from the at least one first portion of the lead lumen when the spring is not compressed.

5. The lead anchor of claim 1 further comprising an actuator capable of compressing the spring.

6. The lead anchor of claim 5, wherein the actuator drives the obstructing member to compress the spring when actuated.

7. The lead anchor of claim 5, wherein the actuator and the obstructing member are unitary.

8. The lead anchor of claim 1 further comprising at least one suture element disposed on the body, the at least one suture element configured and arranged for receiving a suture to suture the lead anchor to patient tissue.

9. The lead anchor of claim 8, wherein the at least one suture element comprises at least one suture opening.

10. The lead anchor of claim 1, wherein the spring is disposed perpendicular the lead lumen.

11. The lead anchor of claim 1, wherein at least a portion of at least one of the body, the obstructing member or the spring is radiopaque.

12. An implantable stimulation device, comprising:
    a lead having an electrode array; and
    the lead anchor of claim 1, coupleable to the lead.

13. The implantable stimulation device of claim 12, further comprising:
    a control module coupleable to the lead.

14. The implantable stimulation device of claim 12, wherein the implantable stimulation device is a spinal cord stimulator.

15. A lead anchor, comprising:
    a body defining at least one first portion of a lead lumen, the body having a first opening and a second opening;
    an obstructing member disposed within the body, the obstructing member defining a second portion of the lead lumen;
    a spring disposed in the body and configured and arranged to operate on the obstructing member so that the second portion of the lead lumen is coterminous with the at least one first portion of the lead lumen and forms a continuous lead path when the spring is compressed and the second portion of the lead lumen is offset from the at least one first portion of the lead lumen when the spring is not compressed, wherein the spring is compressed when the obstructing member is rotated.

* * * * *